United States Patent [19]

Kniep et al.

[11] Patent Number: 5,403,959
[45] Date of Patent: Apr. 4, 1995

[54] PROCESS FOR THE PREPARATION OF 8,N,N-DIALKYLAMINOTRICYCLO-[5.2.2.02.6]DECANE

[75] Inventors: Claus Kniep, Oberhausen; Detlef Kampmann, Gersthofen; Jüger Weber, Oberhausen, all of Germany

[73] Assignee: Hoechst Aktiengesellschaft, Germany

[21] Appl. No.: 226,381

[22] Filed: Apr. 12, 1994

Related U.S. Application Data

[63] Continuation of Ser. No. 992,853, Dec. 16, 1992, abandoned.

[30] Foreign Application Priority Data

Dec. 19, 1991 [DE] Germany .................. 41 41 962.6

[51] Int. Cl.$^6$ ............................................. C07C 209/26
[52] U.S. Cl. .................................................... 564/446
[58] Field of Search .......................... 564/446, 459, 472

[56] References Cited

U.S. PATENT DOCUMENTS

| | | | |
|---|---|---|---|
| 4,190,601 | 2/1980 | Decker et al. | 564/472 |
| 5,225,597 | 7/1993 | Kurek | 564/472 |

FOREIGN PATENT DOCUMENTS

| | | | |
|---|---|---|---|
| 014985 | 9/1980 | European Pat. Off. | |
| 142868 | 5/1985 | European Pat. Off. | 564/472 |
| 62-164653 | 7/1987 | Japan | 564/472 |
| 900456 | 5/1990 | WIPO | C10B 33/34 |

OTHER PUBLICATIONS

Journal of the American Chemical Society, vol. 81, Nr. 3, Feb. 12, 1959 "1,2-Dihydro-endo-di clopentadiene", Wilder Jr. et al., pp. 655–658.

*Primary Examiner*—Glennon H. Hollrah
*Assistant Examiner*—Scott C. Rand
*Attorney, Agent, or Firm*—Jordan B. Bierman

[57] ABSTRACT

A process for the preparation of 8-N,N-dialkylaminotricyclo[5.2.1.0$^{2,6}$]decane by reaction of tricyclo[5.2.1.0$^{2,6}$]decan-8(9)-one with an amine of the formula $HNR_1R_2$, where $R_1$ and $R_2$ are each an alkyl radical having 1 to 6 carbon atoms, in the presence of hydrogen and a platinum-containing supported catalyst, preferably at elevated pressure and elevated temperature.

25 Claims, No Drawings

PROCESS FOR THE PREPARATION OF 8,N,N-DIALKYLAMINOTRICYCLO-[5.2.2.02,6]DECANE

This application is a continuation of application No. 07/992,853, filed Dec. 16, 1992, now abandoned.

This Application claims the priority of German Application P 41 41 962.6, filed Dec. 19, 1991.

The present invention relates to a process for the preparation of 8-N,N-dialkylaminotricyclo[5.2.1.0$^{2,6}$]-decane (hereinafter the Decane). Corresponding quaternary ammonium salts of tricyclo[5.2.1.0$^{2,6}$]decane can be prepared by reacting the Decane with an alkyl halide; these quaternary ammonium salts of tricyclo[5.2.1.0$^{2,6}$]decane are required, for example, for the production of zeolites.

BACKGROUND OF THE INVENTION

A multistage synthesis of 9-dimethylaminotetrahydrodicyclopentadiene (the Decane) is described by P. Wilder, Jr., Ch, F. Culberson, and G. T. youngblood in J. Am. Chem. Soc. 81, 655 to 658 (1959). Starting from a ketone (tricyclo[5.2.1.0$^{2,6}$]decane-8(9)-one), the corresponding oxime is prepared by reaction with hydroxylamine. The oxime is reduced in two separate stages (first by means of PtO$_2$ and H$_2$ and then by means of sodium) to the corresponding amine (8(9)-aminotricyclo[5.2.1.0$^{2,6}$]decane). The amine can be converted to the corresponding (9)-dimethylaminotetrahydrodicyclopentadiene (the Decane) by a mixture of aqueous formaldehyde and formic acid. The yield in the methylation stage is only 48% based on the primary amine employed, and the yield based on the overall preparation process is correspondingly lower.

WO 90/04567 describes a process for preparing N,N-dialkyl-8-aminotricyclo[5.2.1.0]decane (the Decane), starting from 8-ketotricyclo[5.2.1.0]decane (tricyclo[5.2.1.0$^{2,6}$]decan-8(9)-one). In this process the ketone is reacted with a dialkylformamide in the presence of formic acid at temperatures of 160° to 195° C.; the reaction time is 10 to 50 hours. CO$_2$ is formed in the reaction, and has to be removed continuously in order to avoid an undesirable rise in pressure.

The aforedescribed processes are not only technically extremely complex, but are also very time-consuming.

SUMMARY OF THE INVENTION

It is, therefore, an object of the invention to develop a process which is simple to carry out and also enables the Decane to be obtained in high yield, and which, in addition, reduces the time required to carry out the conversion.

This object is achieved by a process for preparing the Decane comprising reacting tricyclo[5.2.1.0$^{2,6}$]decan-8(9)-one with an amine of the formula HNR$_1$R$_2$ where R$_1$ and R$_2$ are each an alkyl radical having 1 to 6 carbon atoms, in the presence of a platinum-containing supported catalyst, with hydrogen at elevated pressure and elevated temperature.

DETAILED DESCRIPTION OF THE INVENTION

The tricyclo [5.2.1.0$^{2,6}$]decan-8(9)-one required for the conversion can be obtained on an industrial scale from dicyclopentadiene. 8(9)-Hydroxytricyclo[5.2.1.0$^{2,6}$]dec-3-ene, which is an unsaturated alcohol, is formed by addition of water in the presence of acid catalysts (H$_2$SO$_4$ or cation exchangers), and can be converted into tricyclo[5.2.1.0$^{2,6}$]decan-8(9)-one by means of a nickel-containing catalyst at elevated temperature. In all probability, this conversion constitutes an intramolecular hydrogen rearrangement, where, in accordance with the following reaction equation, the hydroxyl group in the 8- or 9-position is converted into a keto group with the elimination of hydrogen, and the released hydrogen is added on to the carbon-carbon double bond located at the 3-position.

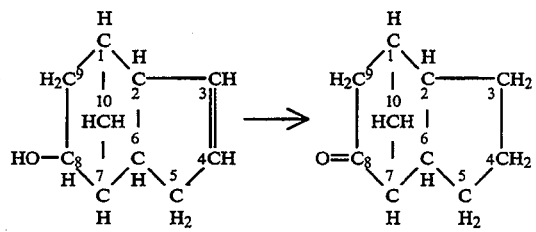

The unsaturated alcohol is in this way converted into tricyclo[5.2.1.0$^{2,6}$]decan-8(9)-one.

According to the following equation:

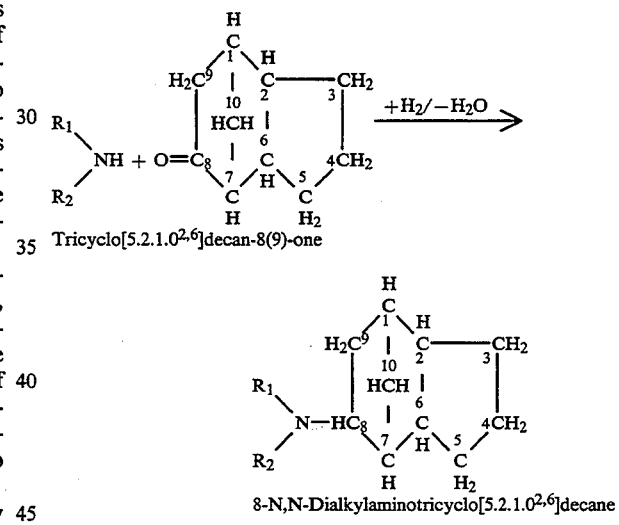

the desired 8-N,N-dialkylaminotricyclo[5.2.1.0$^{2,6}$]decane is formed from tricyclo[5.2.1.0$^{2,6}$]decan-8(9)-one and the amine of the formula R$_1$R$_2$NH.

The starting substances tricyclo[5.2.1.0$_{2,6}$]-decane8(9)-one and the amine of the formula R$_1$R$_2$NH may be used in equivalent amounts. By way of variation, it is also possible to use one of the starting substances in excess. Tricyclo[5.2.1.0$_{2,6}$]-decane8(9)-one and the amine of the formula R$_1$R$_2$NH are normally reacted in a molar ratio of 0.2:1 to 1:1, in particular 0.7:1 to 0.9:1. The radicals R$_1$ and R$_2$ of the amine of the formula R$_1$R$_2$NH may be the same or different, and are desirably an alkyl radical with 1 to 6, especially 1 to 4, preferably 1 to 3, carbon atoms.

Suitable amines are dimethylamine, diethylamine, di-n-propylamine, di-n-butylamine, di-i-butylamine, di-n-pentylamine, di-3-methylbutylamine, di-n-hexylamine, di-i-hexylamine, N-methylethylamine, N-methylpropylamine, N-methylbutylamine, N-methylpentylamine, N-methylhexylamine, N-ethylpropylamine, N-ethylbutylamine, N-ethylpentylamine, N-ethylhexylamine, N-propylbutylamine, N-propylpentylamine, N- propylhexylamine, N-butylpentylamine, and N-butylhexylamine; especially dimethylamine, diethylamine, and di-n-propylamine; and preferably dimethylamine.

The platinum-containing supported catalyst does not have to meet any special requirements as regards platinum content. Catalysts containing 0.1% to 10%, particularly 0.2% to 7%, and preferably 0.5% to 5% by weight of platinum are suitable. Catalysts with a high platinum content may also be used. Suitable supports are kieselguhr, silica gel, $SiO_2$, $Al_2O_3$, or activated charcoal, preferably activated charcoal. Mixtures of the aforementioned substances may also be used as carriers.

The process according to the invention requires the addition of hydrogen. It is recommended that hydrogen be used in excess based on the stoichiometric amount required. It is particularly easy to establish a predetermined pressure by means of hydrogen and then add further hydrogen at the rate at which it is consumed in the conversion. Although the reaction will take place at low pressures, it is recommended to operate at pressures of 0.5 to 15, particularly 1.0 to 10, and preferably 1.5 to 8 MPa.

The conversion starts even at room temperature, but proceeds more rapidly at elevated temperature. Suitable temperatures cover a range from 30° to 150° C., particularly 40 to 130° C., and preferably 50° to 120° C. The process according to the invention can be carried out continuously or batchwise, but is particularly suitable for a batchwise operation.

The following examples illustrate, but do not limit, the invention.

EXAMPLE 1

Preparation of the Decane 2250 g (15 mol) of tricyclo[5.2.1.0$^{2,6}$]decan-8-one and 11.25 g of a catalyst containing 5% by weight of platinum on activated charcoal as a support are introduced, in the absence of oxygen, into a 5 liter autoclave equipped with a rotary stirrer. 877 g (19.5 mol) of dimethylamine are introduced into a separate vessel. The dimethylamine is injected into the autoclave by means of hydrogen, through a capillary connecting the separate, dimethylamine-filled vessel to the autoclave. Hydrogen is then pumped in to a pressure of 1.0 MPa. The reaction mixture is heated to a temperature of 100° C. within 40 minutes, while stirring. The pressure falls to 0.8 MPa as a result of the reaction. The reaction pressure is adjusted to 2.0 MPa by adding hydrogen and is maintained at this level by repeated additions of hydrogen.

After one hour the uptake of hydrogen is complete. The reaction mixture is left to react for a further hour. The reaction product is then cooled and freed from the catalyst by filtration under pressure.

The reaction gives the following results (in each case based on the ketone employed):
Conversion: 96.2% Selectivity: 98.5% yield: 94.8%

EXAMPLE 2

300 g (2 mol) of tricyclo[5.2.1.0$^{2,6}$]decan-8-one and 1.5 g of the catalyst described in Example 1 are introduced, in the absence of oxygen, into a 1 liter autoclave equipped with a rotary stirrer. 117 g (2.6 mol) of dimethylamine are then introduced into a separate vessel. The dimethylamine is injected into the autoclave by means of hydrogen, through a capillary connecting the separate, dimethylamine-filled vessel to the autoclave. The reaction product is then treated as described in Example 1.

The uptake of hydrogen is complete after 55 minutes, and the reaction mixture is left to react for a further hour. The reaction product is then cooled and freed from the catalyst by filtration under pressure.

The reaction gives the following results (in each case based on the ketone employed):
Conversion: 96.5% Selectivity: 98.1% Yield 94.7%

EXAMPLE 3

The procedure as described in Example 2 is followed except that the catalyst of Example 2, after separation by filtration under pressure, is used (first re-use of the catalyst). The uptake of hydrogen is complete after 55 minutes. The reaction mixture is left to react for a further hour. The reaction product is then cooled and freed from the catalyst by filtration under pressure.

The reaction gives the following results (in each case based on the ketone employed):
Conversion: 96.5% Selectivity: 98.2% Yield: 94.8%

EXAMPLE 4

The procedure as described in Example 2 is used, except that the catalyst employed in Example 3 which has been separated by filtration under pressure is used (second re-use of the catalyst). The uptake of hydrogen is complete after 70 minutes, and the reaction mixture is left to react for a further hour. The reaction product is then cooled and freed from the catalyst by filtration under pressure.

The reaction gives the following results (in each case based on the ketone employed):
Conversion: 96.4% Selectivity: 97.8% Yield: 94.3%

The reaction conditions and the composition of the reaction products are determined by gas chromatographic analysis and are given in the following Table.

TABLE

| Example | 1 | 2 | 3 | 4 |
|---|---|---|---|---|
| Temperature [°C.] | 100 | 100 | 100 | 100 |
| Pressure [MPa] | 2.0 | 2.0 | 2.0 | 2.0 |
| Reaction time [min] (including post-reaction) | 120 | 115 | 115 | 130 |
| Starting materials | | | | |
| Ketone[1] [g] | 2250 | 300 | 300 | 300 |
| Dimethylamine [g] | 877 | 117 | 117 | 117 |
| Molar ratio ketone[1]:dimethylamine | 0.77:1 | 0.77:1 | 0.77:1 | 0.77:1 |
| Catalyst (% by wt. of Pt based on ketone) | 0.025 | 0.025 | 0.025 | 0.025 |
| Composition of the reaction product (% by weight) | | | | |
| First runnings | 0.43 | 0.62 | 1.64 | 1.26 |
| Isomers | 0.45 | 0.54 | 0.27 | 0.55 |
| Dimethylaminotricyclodecane[2] | 92.62 | 92.23 | 91.47 | 91.03 |
| Tertiary amines ketone[1] | 0.35 | 0.32 | 0.45 | 0.45 |
| Unsaturated ketone[3] | 3.61 | 3.38 | 3.34 | 3.39 |
| Alcohols[4] | 2.46 | 2.86 | 2.75 | 3.24 |
| Higher boiling point compounds | <0.08 | <0.05 | <0.08 | <0.08 |

[1] Tricyclo[5.2.1.0$^{2,6}$]decan-8-one
[2] 8-N,N-Dialkylaminotricyclo[5.2.1.0$^{2,6}$]decane
[3] Tricyclo[5.2.1.0$^{2,6}$]decan-8-on-3-ene
[4] 8-Hydroxytricyclo[5.2.1.0$^{2,6}$]decane + 8-hydroxytricyclo-[5.2.1.0$^{2,6}$]dec-3-ene While only a limited number of specific embodiments of the present invention have been expressly disclosed, it is, nonetheless, to be broadly construed and not to be limited except by the character of the claims appended hereto.

What is claimed is:

1. A process for the preparation of 8-N,N-dialkylaminotricyclo[5.2.1.0$^{2,6}$]decane which comprises a reaction of tricyclo[5.2.1.0$^{2,6}$]decan-8(9)-one with an amine of the formula $R_1R_2NH$, wherein $R_1$ and $R_2$ are each an alkyl radical, said reaction taking place in the presence of hydrogen and a metallic platinum-containing catalyst on a support.

2. The process of claim 1 wherein said reaction is carried out at elevated pressure.

3. The process of claim 2 wherein said pressure is 0.5 to 15 MPa.

4. The process of claim 3 wherein said pressure is 1.0 to 10 MPa.

5. The process of claim 4 wherein said pressure is 1.5 to 8 MPa.

6. The process of claim 1 wherein said reaction is carried out at elevated temperature.

7. The process of claim 6 wherein said temperature is 30° to 150° C.

8. The process of claim 7 wherein said temperature is 40° to 130° C.

9. The process of claim 8 wherein said temperature is 50° to 120° C.

10. The process of claim 1 wherein said tricyclo[5.2.1.0$^{2,6}$]decan-8(9)-one and said amine are in a molar ratio of 0.2:1 to 1:1.

11. The process of claim 10 wherein said molar ratio is 0.7:1 to 0.9:1.

12. The process of claim 1 wherein each of $R_1$ and $R_2$ is selected from the group consisting of alkyls having 1 to 6 carbon atoms.

13. The process of claim 12 wherein said alkyls have 1 to 4 carbon atoms.

14. The process of claim 13 wherein said alkyls have 1 to 3 carbon atoms.

15. The process of claim 1 wherein said amine is selected from the group consisting of dimethylamine, diethylamine, di-n-propylamine, di-n-butylamine, di-i-butylamine, di-n-pentylamine, di-3-methylbutylamine, di-n-hexylamine, di-i-hexylamine, N-methylethylamine, N-methylpropylamine, N-methylbutylamine, N-methylpentylamine, N-methylhexylamine, N-ethylpropylamine, N-ethylbutylamine, N-ethylpentylamine, N-ethylhexylamine, N-propylbutylamine, N-propylpentylamine, N-propylhexylamine, N-butylpentylamine, and N-butylhexylamine.

16. The process of claim 15 wherein said amine is selected from the group consisting of dimethylamine, diethylamine, and di-n-propylamine.

17. The process of claim 16 wherein said amine is dimethylamine.

18. The process of claim 1 wherein said catalyst contains 0.1% to 10% by weight of platinum.

19. The process of claim 18 wherein said catalyst contains 0.2% to 7.0% by weight of platinum.

20. The process of claim 19 wherein said catalyst contains 0.5% to 5.0% by weight of platinum.

21. The process of claim 1 wherein said support is selected from the group consisting of alumina, kieselguhr, silica gel, silica, activated charcoal, and mixtures thereof.

22. The process of claim 21 wherein said support is selected from the group consisting of alumina, activated charcoal, and mixtures thereof.

23. The process of claim 22 wherein said support is activated charcoal.

24. The process of claim 1 wherein said hydrogen is present in stoichiometric excess.

25. The process of claim 2 wherein said pressure is 1.5 to 8.0 MPa, said reaction being carried out at a temperature of 50° to 120° C., said tricyclo[5.2.1.0$^{2,6}$]decan-8(9)-one and said amine being in a molar ratio of 0.7:1 to 0.9:1, $R_1$ and $R_2$ each having 1 to 3 carbon atoms, said amine being dimethylamine, said catalyst containing 0.5% to 50.% by weight of platinum, said support being activated charcoal, and said hydrogen being present in stoichiometric excess.

* * * * *